United States Patent [19]
Lesins

[11] Patent Number: 5,336,788
[45] Date of Patent: Aug. 9, 1994

[54] METHOD OF MAKING OXYDIPHTHALIC ANHYDRIDE

[75] Inventor: Viesturs Lesins, Buffalo, N.Y.

[73] Assignee: Occidental Chemical Corporation, Niagara Falls, N.Y.

[21] Appl. No.: 151,653

[22] Filed: Nov. 15, 1993

[51] Int. Cl.$^5$ ............................................. C07D 307/89
[52] U.S. Cl. ..................................... 549/241; 549/250
[58] Field of Search .......................................... 549/241

[56] References Cited

U.S. PATENT DOCUMENTS

| | | | |
|---|---|---|---|
| 4,808,731 | 2/1989 | Berdahl et al. | 549/241 |
| 5,021,168 | 6/1991 | Molinaro et al. | 549/241 |
| 5,077,415 | 12/1991 | Jasne et al. | 549/241 |
| 5,145,971 | 9/1992 | Lesins | 549/241 |
| 5,153,335 | 10/1992 | Stults | 549/241 |

Primary Examiner—Cecila Tsang
Attorney, Agent, or Firm—Wayne A. Jones; Richard D. Fuerle

[57] ABSTRACT

Disclosed is a method of making oxydiphthalic anhydride from oxydiphthalic acid. The oxydiphthalic acid is mixed with an organic liquid that codistills with water and the resulting slurry is heated to the boiling point of the slurry to remove any water. About 1 to about 4 moles of acetic anhydride per mole of oxydiphthalic acid are added to the slurry and the slurry is heated to a temperature between 50° and 160° C. until the oxydiphthalic acid content thereof is less than 0.1 weight percent. The slurry is filtered and the filter cake is heated to a temperature between about 180° C. and below its melting point for about 12 to about 24 hours.

20 Claims, No Drawings

METHOD OF MAKING OXYDIPHTHALIC ANHYDRIDE

BACKGROUND OF THE INVENTION

This invention relates to a method of making oxydiphthalic anhydride (ODPA) from oxydiphthalic acid (ODTA). In particular, it relates to the use of both heat and acetic anhydride to obtain a virtually complete reaction of ODTA to ODPA in a short time without degradation of the ODPA.

ODPA is used to make polyimides and other chemical products. In certain applications, such as in the electronics industry, it is necessary for these products to have a low level of impurities, especially of ionic impurities. The purification of ODPA can be accomplished by converting the ODPA to ODTA, then reconverting the ODTA back to ODPA.

The conversion of ODPA to ODTA is relatively simple and it occurs readily with the addition of water. ODTA is almost insoluble in the water, but most impurities, especially ionic impurities, are soluble, and in this way they can be separated from ODTA. It is the conversion of the ODTA back to ODPA that presents the problems.

The conversion of ODTA to ODPA can be accomplished by heating ODTA to a temperature below its melting point (227° C.). However, conversions below the melting point cannot be completed in a reasonable time. If the conversion is incomplete, a small amount, less than 1 wt %, of a compound known as oxydiphthalic diacid (ODDA) is produced. In ODDA one of the diacid groups of ODTA is converted to anhydride while the other diacid group remains a diacid. In the polymerization of the ODPA with a comonomer such as a diamine (to make a polyimide), the ODDA acts as a chain terminator, resulting in low molecular weight polymer of inferior properties. Thus, it is necessary to reduce the ODDA content of the ODPA to below the detectable limit of about 0.05 wt % in order to produce high molecular weight polymers.

This can be accomplished in one of four ways. First, the ODTA can be heated at very close to its melting point for a long time. However, this requires careful temperature control in order to avoid going over the melting point and the length of time required is so long that it may be impractical for most industrial purposes. Second, the ODTA can be heated above its melting point. However, this can cause degradation of the ODPA which can also result in lower molecular weight polymers. The third method is to react the ODTA with a large excess of a dehydrating agent such as acetic anhydride (see, for example, U.S. Pat. No. 4,808,731). Acetic anhydride dehydrates ODTA chemically as it reacts with ODTA to form ODPA and acetic acid. The problem with this method is that 8 moles or more of excess acetic anhydride must be employed. The unreacted acetic anhydride must then be recovered, disposed of, or further processed, which adds additional costs to the process. If less than the stoichiometric amount (i.e., two moles/mole of ODTA) of acetic anhydride is used, of course, only a portion of the ODTA will be converted to ODPA.

Another problem with the use of acetic anhydride is its harmful effects. Even when exhaustively dried, the undesirable odor of acetic anhydride lingers with ODPA that is cyclized in acetic anhydride. Furthermore, the odor detection limit of acetic anhydride in air is reported to be 0.14 to 0.36 ppm, and since the Occupational Safety and Health Administration (OSHA) permissible exposure limit is 5 ppm, potential health hazards exist because there is only a small concentration window in which the odor can be detected at a level considered safe.

A fourth method of converting ODTA to ODPA is to recrystallize ODTA in a high boiling solvent such as 1,2-dichlorobenzene. ODTA would be refluxed in the solvent. As cyclization occurs, water is taken off overhead. When the solution clears, the cyclization is complete and the solution can be cooled to crystallize ODPA which is then recovered by filtration. The ODPA filter cake must then be dried to remove the solvent. The problem is that residual solvent remains with the ODPA, particularly when the solvent is dichlorobenzene (DCB), and the process can take 8 hours or more.

SUMMARY OF THE INVENTION

I have discovered that, while heating ODTA to a temperature below its melting point for a reasonable time will not completely convert it to ODPA and, while reacting the ODTA with less than a stoichiometric amount of acetic anhydride will not convert all of the ODTA to ODPA, if the ODTA is heated to a temperature below its melting point for a short time after treatment with less than 2 moles of acetic anhydride (per mole of ODTA), virtually all of the ODTA is converted to ODPA. Since the ODTA is not melted, the degradation that occurs above the melting point is avoided. And, since less than 2 moles of acetic anhydride are used, the problems associated with excess acetic anhydride are reduced or avoided. In other words, while heating alone does not produce a complete conversion in a short time, and less than a stoichiometric amount of acetic anhydride does not produce a complete conversion, the two together act synergistically to produce a virtually complete conversion of the ODTA to ODPA. This synergistic interaction was unexpected and was not predicted in the literature.

I have also found that less ODDA is also produced if the amount of acetic anhydride is slightly in excess of stoichiometric. While this procedure does leave some unreacted acetic anhydride, the amount is small enough to be removed by solvent washing.

DESCRIPTION OF THE INVENTION

The ODTA starting material for this invention is not a commercially available product, but it is easily obtained from ODPA, which is a commercial product. ODPA is reacted with water to forth the water-insoluble ODTA which is then filtered. The resulting ODTA is thus wet with water which must be removed, or at least accounted for, because it reacts with acetic anhydride. The water is easily removed by techniques well-known to those skilled in the art. For example, the water wet ODTA could be placed in a heated oven to remove the water or the wet ODTA can be washed with a liquid in which it is insoluble but in which water is soluble, such as acetic acid.

The dry or slightly wet ODTA is mixed with an organic liquid in which ODPA and ODTA have low solubility, thereby forming a slurry. The organic liquid preferably boils at about 50° to about 227° C. and codistills with water. Codistillation is then conducted at a temperature of, for example, about 100° to about 120°

C., which typically takes about an hour. Suitable organic liquids include toluene, xylene, and various long-chain hydrocarbons such as hexane. The preferred organic liquid is toluene, which codistills with water at about 113° C. Toluene is preferred because the boiling point at which codistillation occurs is close to the preferred temperature of reaction with the acetic anhydride, about 100° C., so that only a little cooling is necessary. Liquid toluene and water are easily separated so that the toluene portion of the distillate can be decanted from the water portion and returned to the reaction vessel to again remove water. In addition, since water has a low solubility in toluene, the loss of acetic anhydride values by reaction with water is minimized. Also, acetic anhydride is soluble in toluene which results in a faster reaction between the ODTA and the acetic anhydride. Sufficient organic liquid should be used so that, after removal of the water, a slurry remains that is about 5 to about 50 wt % solids. At less than 5 wt % solids the reactor volume is being wasted and at more than 50 wt % solids it is difficult to stir the slurry; preferably the slurry is about 15 to about 40 wt % solids.

In the next step of the process of this invention, acetic anhydride is added to the slurry. Propionic anhydride can be used in addition to or instead of acetic anhydride but acetic anhydride is preferred as it is less expensive and more readily available. It is preferable to cool the slurry slightly below its boiling point before adding acetic anhydride so that the acetic anhydride does not reflux into the headspace where trace quantities of water could exist which would consume acetic anhydride. Preferably, less than 2 moles of acetic anhydride are used per mole of ODTA in order to avoid having excess acetic anhydride in the ODPA product. However, at least 1 mole of acetic anhydride per mole of ODTA should be used for an efficient reaction, and it is preferable to use 1.4 to 1.99 moles of acetic anhydride per mole of ODTA. In an alternative less preferred procedure, about 2 to about 4 moles (up to 1.5 equivalents) of acetic anhydride is added per mole of ODTA. Even at a ratio of 4 moles of acetic anhydride per mole of ODTA complete cyclization of the ODTA will not occur in the absence of heat.

The reaction of the ODTA with the acetic anhydride typically requires about 1 to about 4 hours at a temperature of about 50° to about 160° C. Below a temperature of 50° C. the reaction is too slow and at a temperature over 160° C. degradation of the ODPA may occur. It is preferable to use a temperature of about 90° to about 110° C. In this invention, cyclization is less than 95% in this initial reaction step, but cyclization in the initial reaction stage is greater when the acetic anhydride/ODTA ratio is higher.

Based on the starting conditions, individuals skilled in the art can determine the necessary time of reaction or the reaction can be followed by liquid chromatography. The reaction is terminated when the rate of conversion of ODTA to ODPA becomes unacceptably slow. The acetic acid produced in the reaction with acetic anhydride (or propionic acid if propionic anhydride is used) is soluble in the toluene but the ODPA is not.

The slurry is cooled to room temperature and is filtered. The filter cake is washed with toluene to remove any remaining acetic acid or unreacted acetic anhydride. If desired, the acetic acid and acetic anhydride in the toluene filtrate can be recovered by a variety of methods including, for example, distillation, extraction, or reaction and precipitation.

As a last step, the filter cake is dried by heating at about 180° C. up to (but below) its melting point (about 227° C.) for about 12 to about 24 hours. This step is necessary to complete the cyclization of the ODTA.

The following examples further illustrate this invention.

EXAMPLE 1-COMPARATIVE EXAMPLE

This shows the relationship between the time and temperature at which ODTA is heated and the percent conversion of the ODTA to ODPA. Samples of ODTA were heated for 15 hours at various temperatures and other samples were heated for 63 hours at various temperatures and the weight percent ODTA in the resulting ODPA (calculated by titrating the water of cyclization released when the samples are melted) was determined. The following table gives the results of these experiments. In the table, the results are an average of three runs.

| Time (hrs) | Temperature (°C.) | Oven A (% ODTA) | Oven B (% ODTA) |
|---|---|---|---|
| 63 | 184 | | 0.36 |
| | 192 | 0.38 | |
| | 222 | 0.15 | 0.18 |
| | 225 | 0.11 | 0.10 |
| 15 | 192 | 0.49 | 0.53 |
| | 215 | 0.34 | 0.38 |
| | 222 | | 0.27 |
| | 225 | 0.24 | 0.21 |

The above table shows that at a time of 15 hours the ODPA that was produced was too contaminated with ODTA. Even at a time of 63 hours and a temperature of 225° C., which is very close to the melting point of 227° C., the samples still contain 0.1 wt % ODTA.

EXAMPLE 2-COMPARATIVE

To a 100 mL round bottom flask was charged 10.2063 g of ODTA. The flask was fitted such that a nitrogen purge of approximately 250 sccm could be continuously introduced. The flask was placed in a preheated oil bath and heated to approximately 255° C. The oil bath temperature was maintained in the 255° C. to 257° C. range over a course of 4 hours. After the 4 hour hold period at a nominal temperature of 260° C., the flask was removed from the oil bath and the molten ODPA was allowed to cool. A similar experiment was performed in which the ODPA was heated to approximately 185° C. and held for 6 hours. The transmission at 430 nm of a 8.4 wt % ODPA solution in 1-methyl-2-pyrrolidinone solvent was determined. Analytical results for the thermally treated ODPA are shown in the following table.

| Nominal Hold Temperature (°C.) | ODPA Melted? | Nominal Hold Time (hours) | % ODTA | % Transmission |
|---|---|---|---|---|
| 215 | No | 6 | 0.3 | 75.8 |
| 260 | Yes | 4 | ND 0.1 | 43.2 |

The table shows that, while melting reduces ODTA below the detection limit, the lower % transmission indicates that melting has also degraded the ODPA.

EXAMPLE 3

To a 250 mL three-necked flask equipped with a water cooled condenser, magnetic stir bar, combination hot platemagnetic stirrer, and nitrogen pad, was charged 9.97 g ODTA (28.8 mmol), 91.20 g toluene, and 5.82 (57.0 mmol) of acetic anhydride. This is a mole ratio of acetic anhydride to ODTA of 1.99. The resulting slurry was heated to reflux and held at reflux for 4 hours. The solution was allowed to cool to room temperature over the course of the next 3 to 4 hours.

The resulting slurry was filtered to recover the solids with an additional 24.2 g of fresh toluene used to rinse the flask and wash the filter cake. The wet solids were placed in a 140° C. air circulating oven to dry for 24 hours. The dried cake was removed from the oven and split into two samples. Sample A was retained for analysis whereas Sample B was returned to the oven to thermally treat the sample an additional 24 hours at 200° C.

As a control, a small aliquot of ODTA was also placed in the same oven to dry for 24 hours at 140° C. The control sample was also split into 2 samples, referred to as Control A and Control B. Control A was retained for analysis and Control B was returned to the 200° C. oven along with Sample B. Liquid chromatographic analysis of the oven dried samples is summarized in the following table:

| Identification | Acetic Anhydride | Thermal Treatment | Product (area %) ODDA | ODTA | % Cyclization |
|---|---|---|---|---|---|
| Sample B | X | X | 0.2 | ND 0.05 | 99.9 |
| Sample A | X |   | ND 0.1 | 56.6 | 44.4 |
| Control B |   | X | 0.9 | ND 0.05 | 99.6 |
| Control A |   |   | ND 0.1 | >99 | <1 |

NDX = not detected at a detection level of X

The table shows that at a molar ratio of acetic anhydride to ODTA of less than 2 to 1 only partial cyclization occurs. Acetic anhydride alone does not result in adequate cyclization (Sample A). Thermal cyclization (Control B) results in ODPA that contains 0.9 area % ODDA. When acetic anhydride and thermal cyclization are used together (Sample B) a significant reduction in the level of ODDA to 0.2% occurs.

EXAMPLE 4

ODTA, 20 grams, was refluxed at 113° C. with 8.85 grams of acetic anhydride in 71.10 grams of toluene for 6 hours. The slurry was then cooled and filtered to recover the solid filter cake which was washed with 20 grams of toluene. The filter cake was placed in an oven at 190° to 200° C. The dried filter cake was analyzed for ODTA which was found to be below the detection limit of 0.1% by weight.

EXAMPLE 5

ODPA was reacted with water to produce ODPA according to the process described in U.S. Pat. No. 5,145,971. The water and the wet ODTA filter cake (75.2 g, 80.7 wt % ODTA, 175 mmol ODTA) was added to 74.8 grams of toluene. The resulting slurry was heated to reflux for about 1.25 hours to remove the water. Approximately 7.0 mL of an aqueous phase was apparent in the moisture receiver. The slurry was cooled to about 80° C. and 32.1 grams of acetic anhydride (314 mmols) was added. The slurry was heated to about 105° C. and heating was continued at that temperature for about 4 hours. The slurry was cooled to about 40° C. and filtered to recover the filter cake, which was washed with 120 grams of toluene. After drying 15 hours in an oven at 185° C., the filter cake was analyzed for ODTA and it was found that the ODTA content was below the detection limit of 0.1%.

EXAMPLE 6

To a 125 mL three-necked flask equipped with a water cooled condenser, magnetic stir bar, combination hot plate/magnetic stirrer, thermometer, Dean & Stark moisture receiver, and nitrogen pad, was charged 9.48 g ODTA (27.4 mmol) and 99.86 g of mixed xylenes. The resulting slurry was heated to reflux (approximately 138° C.) and held at reflux for 6 hours. The solution was allowed to cool to room temperature. At no point in time was any sign of moisture observed in the moisture receiver, indicating that cyclization did not take place.

The resulting slurry was filtered to recover the solids. An additional 28.51 g of fresh mixed xylenes was used to rinse the flask and wash the filter cake. The wet solids were placed in a 140° C. air circulating oven to dry for 24 hours. The dried cake (9.17 g) was removed from the oven and analyzed by liquid chromatography. The analysis revealed the sample was below the detection limit of 0.1% for ODDA and 96.3±3 weight % ODTA.

This example shows that cyclization will not occur thermally at temperatures below about 140° C. in or out of solvent.

EXAMPLE 7-COMPARATIVE

ODTA was added to toluene and acetic anhydride was added to the resulting slurry. The slurry was heated to reflux and refluxed for approximately 4 hours. The slurry was allowed to cool to about 35° C. at which time the slurry was filtered to recover the solids. The solids were washed twice with 15 g aliquots of the fresh toluene used to rinse the flask. The resulting two filter cakes were split and dried in separate air circulating ovens at two different temperatures. Analysis of the dried samples are summarized in the following tables.

| Run | ODTA (g) | Toluene (g) | Acetic Anhydride (g) | Acetic Anhydride/ ODTA Mole Ratio |
|---|---|---|---|---|
| A | 10.2 (29.5 mmol) | 85.7 | 12.5 (122 mmol) | 4.15:1 |
| B | 10.3 (29.8 mmol) | 73.8 | 24.3 (238 mmol) | 7.99:1 |

|  | Run A | | Run B | |
|---|---|---|---|---|
| Drying Temperature | % ODDA | % ODTA | % ODDA | % ODTA |
| 140° C. | 0.10 | 0.14 | 0.06 | ND 0.05 |
| 200° C. | 0.05 | ND 0.05 | ND 0.05 | ND 0.05 |

The tables show that complete cyclization of ODTA to ODPA did not occur in 4 hours with 208% or 399% of the theoretical stoichiometric amount of acetic anhydride required for ODTA cyclization.

I claim:

1. A method of making oxydiphthalic anhydride from dry oxydiphthalic acid comprising
(A) forming a slurry of said oxydiphthalic acid with an organic liquid;
(B) adding to said slurry about one to about 4 moles of acetic anhydride or propionic anhydride per mole of oxydiphthalic acid;
(C) heating said slurry to a temperature between 50° C. and the boiling point of said organic liquid; and
(D) exposing the solids from said slurry to a temperature between about 180° C. and the melting point of said solids for a time sufficient to reduce the oxydiphthalic acid content of said solids to less than 0.1 wt %.

2. A method according to claim 1 wherein the molar ratio of acetic anhydride or propionic anhydride to oxydiphthalic acid is 1.4 to 1.99.

3. A method according to claim 1 wherein said solids are separated from said slurry and are washed with toluene before step (D).

4. A method according to claim 2 wherein the molar ratio of acetic anhydride or propionic anhydride to oxydiphthalic acid to 2 to about 4.

5. A method according to claim 1 wherein said organic liquid boils at about 50° to about 227° C. and said solids are separated from said slurry before they are exposed to said temperature in step (D).

6. A method according to claim 5 wherein said organic liquid is toluene.

7. A method according to claim 5 wherein said slurry is heated at about 90° to about 110° C. in step (C).

8. A method according to claim 5 wherein in step (C) said slurry is heated for about 1 to about 4 hours.

9. A method according to claim 1 wherein said slurry is about 5 to about 50 weight percent solids.

10. A method according to claim 9 wherein said slurry is about 15 to about 40 weight percent solids.

11. A method according to claim 1 wherein said oxydiphthalic acid is obtained by reacting oxydiphthalic anhydride with water and said water is removed prior to step (A).

12. A method according to claim 11 wherein said water is removed by adding acetic acid to said oxydiphthalic anhydride and heating to codistill said water and said acetic acid.

13. A method according to claim 12 wherein said liquid with which water codistills is toluene.

14. A method of making oxydiphthalic anhydride from wet oxydiphthalic acid comprising
(A) mixing said oxydiphthalic acid with a sufficient amount of an organic liquid with which water codistills at a temperature of about 90° to about 110° C., to form a slurry of about 5 to about 50 weight percent solids;
(B) heating said slurry to codistill said water and said organic liquid;
(C) adding to said slurry 1.4 to 4.0 moles of acetic anhydride per mole of said oxydiphthalic acid;
(D) heating said slurry at about 90° to about 110° C.; and
(E) filtering said slurry, washing the filter cake, and drying the filter cake at a temperature between about 180° C. and below its melting point for about 12 to about 24 hours.

15. A method according to claim 14 wherein the ratio of acetic anhydride to oxydiphthalic acid is 1.4 to 1.99.

16. A method according to claim 14 wherein said slurry is about 15 to about 40 weight percent solids.

17. A method according to claim 14 wherein the ratio of acetic anhydride to oxydiphthalic acid is 2 to 4.

18. A method according to claim 14 including the initial step of reacting oxydiphthalic anhydride with water to produce said oxydiphthalic acid.

19. A method according to claim 14 wherein in step (D) said slurry is heated for about 1 to about 4 hours.

20. A method of making oxydiphthalic anhydride from water wet oxydiphthalic acid comprising
(A) mixing said oxydiphthalic acid with a sufficient amount of toluene to form a slurry of about 15 to about 40 weight percent solids;
(B) heating said slurry at about 90° to about 110° C. to codistill said water and said toluene;
(C) adding to said slurry about 1.4 to about 1.99 moles of acetic anhydride per mole of said oxydiphthalic acid;
(D) heating said slurry at about 90° to about 110° C. for about 1 to about 4 hours;
(E) filtering said slurry and washing the filter cake with toluene; and
(F) drying the filter cake at a temperature between about 180° C. and below its melting point for about 12 to about 24 hours.

* * * * *